United States Patent
Tamura et al.

(10) Patent No.: US 6,521,806 B1
(45) Date of Patent: *Feb. 18, 2003

(54) PROCESS FOR PRODUCING 1-HEXENE

(75) Inventors: Mitsuhisa Tamura, Chiba-ken (JP);
Kenshi Uchida, Chiba-ken (JP);
Kiyoshi Iwanaga, Chiba-ken (JP);
Yoshiaki Ito, Chiba-ken (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1182 days.

(21) Appl. No.: 08/521,432

(22) Filed: Aug. 30, 1995

(30) Foreign Application Priority Data

Sep. 5, 1994 (JP) .............................. 6-211457
Nov. 2, 1994 (JP) .............................. 6-269845
Jun. 8, 1995 (JP) .............................. 7-141629

(51) Int. Cl.$^7$ ................................. C07C 2/24
(52) U.S. Cl. .................. 585/512; 585/511; 585/513
(58) Field of Search ................. 585/505, 511, 585/512, 513

(56) References Cited

U.S. PATENT DOCUMENTS

| | | | |
|---|---|---|---|
| 4,668,838 A | 5/1987 | Briggs | 585/513 |
| 5,376,612 A | 12/1994 | Reagen et al. | |
| 5,382,738 A | 1/1995 | Reagen et al. | 585/512 |
| 5,438,027 A | 8/1995 | Reagen et al. | |
| 5,451,645 A | 9/1995 | Reagen et al. | |
| 5,491,272 A | 2/1996 | Tanaka et al. | |
| 5,523,507 A | * 6/1996 | Reagen et al. | 585/513 |
| 5,750,817 A | * 5/1998 | Tanaka et al. | 585/512 |
| 5,811,618 A | * 9/1998 | Wu | 585/513 |
| 5,910,619 A | * 6/1999 | Urata et al. | 585/513 |

FOREIGN PATENT DOCUMENTS

| | | |
|---|---|---|
| EP | 0416304 | 3/1991 |
| EP | 0537609 | 4/1993 |
| EP | 0608447 | 8/1994 |
| EP | 0611743 | 8/1994 |
| EP | 0614865 | 9/1994 |
| EP | 0622347 | 11/1994 |
| EP | 0668105 A2 | 8/1995 |
| GB | 1181713 | 2/1970 |
| JP | 6-157655 | 6/1994 |

* cited by examiner

Primary Examiner—Wayne A. Langel
(74) Attorney, Agent, or Firm—Sughrue Mion, PLLC

(57) ABSTRACT

A process for preparing 1-hexene which comprises trimerizing ethylene in a 1-hexene solvent in the presence of a catalyst system prepared by contacting in a 1-hexene solvent the following components (A), (B), (C) and (D):

(A) a chromium-containing compound represented by the general formula: $CrX_kY_m$ wherein X is a residue of a carboxylic acid, a residue of a 1,3-diketone, a halogen atom or an alkoxyl group, k is an integer of 2 to 4, Y in $Y_m$ is an amine compound, a phosphine compound, a phosphine oxide compound, a nitrosyl group or an ether compound and m is an integer of 0 to 6, with the proviso that any two Y's may be same or different;

(B) trialkylaluminum or dialkylaluminum hydride;

(C) a pyrrole compound or a derivative thereof;

(D) a group 13 (IIIB)-halogen compound represented by the general formula: $MT_tU_{3-t}$ or a group 14 (IVB)-halogen compound represented by the general formula: $M'T'_{t'}U_{4-t'}$ wherein M is an atom from the group 13 (IIIB), M' is an atom from the group 14(IVB), T is an alkyl group, an aryl group, an allyl group or a hydrogen atom, U is a halogen atom, t is a real number of 0 or more and less than 3 and t' is a real number of 0 or more and less than 4.

8 Claims, No Drawings

PROCESS FOR PRODUCING 1-HEXENE

BACKGROUND OF THE INVENTION

1. Field of the Invention

The present invention relates to a process for producing 1-hexene.

2. Background Information

The following processes have been known as the processes for producing 1-hexene by trimerization of ethylene.

Thus, U.S. Pat. No. 4,668,838 discloses a process in which a chromium compound, a hydrocarbyl aluminum hydrolyzed with about 0.8 to about 1.1 mole of water per mole of an aluminum compound and a donor ligand were used as a catalyst. This process, however, had defects that the catalyst was insufficient in activity and selectivity and that maintenance of the activity of the catalyst was uneasy.

EP 0 537 609 and EP 0 622 347 disclose processes in which a chromium complex and an aluminoxane were used as a catalyst. These processes were also unsatisfactory due to insufficient activity and selectivity of the catalyst.

EP 0 611 743 discloses a process in which a chromium compound, an alkylaluminum compound and an amine or a metal amide were used as a catalyst. The process was also unsatisfactory due to insufficient activity and selectivity of the catalyst.

Further, JP-A-6-157655 discloses a process in which a chromium compound, an aluminum compound and a pyrrole compound were used as a catalyst, and EP 0 608 447 discloses a process in which a chromium compound, an aluminum compound, a pyrrole compound and a halogen compound were used as a catalyst. These processes, however, had defects that an apparatus and an excess energy were required for a separation step of 1-hexene, the desired product, and a solvent, which step was necessary because they used other solvent except 1-hexene.

As a result of an extensive study, conducted by the present inventors, on a process for producing 1-hexene which is not suffered from the above defects, it has been found that 1-hexene can be produced with excellent industrial efficiency, maintaining selectivity of the trimer C6–compound and purity of 1-hexene in the C6-compound at a superior level and without requiring an apparatus and energy for separating the desired 1-hexene and a solvent, by trimerizing ethylene using a catalyst comprising a chromium-containing compound, an aluminum compound, a pyrrole compound and a group 13(IIIB)-halogen compound or a group 14(IVB)-halogen compound and using the desired compound 1-hexene as a solvent. The present invention has been accomplished on the basis of such finding.

SUMMARY OF THE INVENTION

Accordingly, the present invention provides a process for producing 1-hexene which comprises trimerizing ethylene in a 1-hexene solvent in the presence of a catalyst system prepared by contacting in a 1-hexene solvent the following components (A), (B), (C) and (D):

(A) a chromium-containing compound represented by the general formula: $CrX_kY_m$ wherein X in $X_k$ is a residue of a carboxylic acid, a residue of a 1,3-diketone, a halogen atom or an alkoxyl group, k is an integer of 2 to 4, Y in $Y_m$ is an amine compound, a phosphine compound, a phosphine oxide compound, a nitrosyl group or an ether compound and m is an integer of 0 to 6, with the proviso that any two Y's may be same or different;

(B) trialkylaluminum or dialkylaluminum hydride;

(C) a pyrrole compound or a ;derivative thereof;

(D) a group 13 (IIIB)-halogen compound represented by the general formula: $MT_tU_{3-t}$ or a group 14 (IVB)-halogen compound represented by the general formula: $M'T'_{t'}U_{4-t'}$ wherein M is an atom from the group 13 (IIIB), M' is an atom from the group 14(IVB), T is an alkyl group, an aryl group, an allyl group or a hydrogen atom, U is a halogen atom, t is a real number of 0 or more and less than 3 and t' is a real number of 0 or more and less than 4.

DETAILED DESCRIPTION OF THE INVENTION

The present invention will be described in more detail in the following.

The component (A) of the catalyst used in the present invention is a chromium compound represented by the general formula: $CrX_kY_m$.

In the component (A), X. in $X_k$ is a residue of a caarboxylic acid, a residue of a 1,3-diketone, a halogen atom or an alkoxyl group and k is an integer of 2 to 4. Y in $Y_m$ is an amine compound, a phosphine compound, a phosphine oxide compound, a nitrosyl group or an ether compound and m is an integer of 0 to 6. It is to be noted that any two Y's may be same or different.

The residue of the carboxylic acid having 1 to 20 carbon atoms is preferred and includes, for example, residues of 2-ethylhexanoic acid, naphthenic acid, acetic acid, hydroxy-2-ethylhexanoic acid, dichloroethylhexanoic acid, butyric acid, neopentanoic acid, lauric acid, stearic acid, oxalic acid and the like, whereby the residues of 2-ethylhexanoic acid and naphthenic acid are preferred.

The residue of the 1,3-diketone having 5 to 20 carbon atoms is preferred and includes, for example, residues of acetylacetone, 2,2,6,6-tetramethyl-3,5-heptanedione, 1,1,1-trifluoroacetylacetone., benzoylacetone and the like.

The halogen atom includes chlorine, bromine, iodine and fluorine, whereby chlorine is preferred.

The alkoxyl group having 1 to 20 carbon atoms is preferred and includes, for example, t-butoxy group, isopropoxy group and the like.

The amine compound includes, for example, ammonia, ethylenediamine, diethylenetriamine, pyridine, pyridine derivatives, isoquinoline, isoquinoline derivatives, aniline and the like.

The pyridine derivatives include 4-dimethylaminopyridine, 4-cyanopyridine, 2-picoline, 3-picoline, 4-picoline, 2-ethylpyridine, 3-ethylpyridine, 4-ethylpyridine, 2-propylpyridine, 4-propylpyridine, 4-isopropylpyridine, 3-butylpyridine, 4-butylpyridine, 4-isobutylpyridine, 4-t-butylpyridine, 2-phenylpyridine, 3-phenylpyridine, 4-phenylpyridine, 2-benzylpyridine, 4-benzylpyridine, 4-phenylpropylpyridine, 4-(5-nonyl) pyridine, 3-(4-pyridyl)-1,5-diphenylpentane, 2-vinylpyridine, 4-vinylpyridine, 4-butenylpyridine, 4-(1-propenylbutenyl)pyridine, 4-pentenylpyridine, 4-(1-butenylpentenyl)pyridine, 2,6-lutidine, 2,4-lutidine, 2,5-lutidine, 3,4-lutidine, 3,5-lutidine, 2-methyl-4-ethylpyridine, 2-methyl-5-ethylpyridine, 3-methyl-4-ethylpyridine, 3-ethyl-4-methylpyridine, 3,4-diethylpyridine, 3,5-diethylpyridine, 2-methyl-5-butylpyridine, 2,6-dipropylpyridine, 2,6-di-t-butylpyridine, 2,6-diphenylpyridine, 2,3-cyclopentenopyridin e, 2,3-cyclohexenopyridine, 2-methyl-G-vinylpyridine, 5-ethyl-2- vinylpyridine, 2,4,6-collidine, 2,3,5-collidine, 2-methyl-3-ethyl-6-propylpyridine, 2,6-di-t-butyl-4-methylpyridine and the like.

The isoquinoline derivatives include 1-methylisoquinoline, 3-methylisoquinoline, phenanthridine and the like.

The phosphine compound include, for example, tributylphosphine, triphenylphosphine and the like.

The phosphine oxide compound includes tributylphosphine oxide, triphenylphosphine oxide and the like.

The ether compound includes tetrahydrofuran and the like.

Specific examples of the component (A) includes trichlorotris(ethylenediamine) chromium(III) 3.5 hydrate, trichlorotris(4-dimethylaminopyridine) chromium(III), trichlorotripyridine chromium(III), trichlorotri(4-ethylpyridine) chromium(III), trichlorotri(4-isopropylpyridine) chromium(III), trichlorotri-(4-t-butylpyridine) chromium(III), trichlorotri(4-phenylpyridine) chromium(III), trichlorotri(4-phenylpropylpyridine) chromium(III), trichlorotri(4-(5-nonyl)-pyridine) chromium(III), trichlorotri(3,5-lutidine) chromium(III), tribromotripyridine chromium(III), trifluorotripyridine chromium(III), dichlorobis(pyridine) chromium(II), dibromobis(pyridine) chromium(II), trichlorotriisoquinoline chromium(III), trichlorotrianiline chromium(III), trichlorotritetrahydrofuran chromium(III), chromium(III) tris(2-ethylhexanoate), chromium(II) bis(2-ethylhexanoate), chromium(III) tris(naphthenate), chromium(II) bis(naphthenate), chromium(III) tris(acetate), chromium(II) bis(acetate), chromium(III) tris(acetylacetona te), chromium(II) bis(acetylacetonate), chromium(III) tris(2,2,6,6-tetramethyl-3,5-heptadionate), chromium(IV) tetra(t-butoxide), dichlorodinitrosylbis(triphenylphosphineo xide) chromium , dichlorobis (triphenylphosphineoxide) chromium(II), dichlorodinitrosylbis(4-ethylpyridine) chromium trichlorobis(tributylphosphine) chromium(III) dimer, trichloro(1,4,7-trimethyl-1,4,7-triazacyclononane chromium(III) and the like.

In particular, trichlorotris(ethylenediamine) chromium (III) 3.5 hydrate, trichlorotris(4-dimethylaminopyri dine) chromium(III), trichlorotripyridine chromium(III), trichlorotri(4-ethylpyridine) chromium(III), trichlorotri(4-isopropylpyridine) chromium(III), trichlorotri(4-t-butylpyridine) chromium(III), trichlorotri(4-phenylpyridine) chromium(III), trichlorotri(4-phenylpropylpyridine) chromium(III), trichlorotri(4-(5-nonyl)-pyridine) chromium(III), trichlorotri(3,5-lutidine) chromium(III) trichlorotriisoquino line chromium(III) are preferred.

As the component (A) of the present invention, the components in which X is a halogen atom and k is 2 or 3 are particularly preferred.

The component (B) of the catalyst used in the present invention includes trialkylaluminum or dialkylaluminum hydride.

The alkyl group in the component (B) is exemplified by methyl group, ethyl group, propyl group, isopropyl group, butyl group, isobutyl group, hexyl group, octyl group and the like.

Specific examples of the component (B) includes trimethylaluminum, triethylaluminum, tripropylaluminum, tributylaluminum, triisobutylaluminum, trihexylaluminum, trioctylaluminum, diethylaluminum hydride, diisobutylalu- min um hydride and the like, whereby triethylaluminum is particularly preferred.

The component (C) of the catalyst used in the present invention includes pyrrole compound and derivatives thereof.

Specific examples of the component (C) includes pyrrole, 2, 5-dimethylpyrrole, 2,5-diethylpyrrrole, 2,5-dipropylpyrrole, 2-methylpyrrole, 2-ethylpyrrole, 3-methylpyrrole, 3-ethylpyrrole, 3-propylpyrrole, 3-butylpyrrole, 3-heptylpyrrole, 3-octylpyrrole, 3-ethyl-2,4-dimethylpyrrole, 2,3,4,5-tetramethylpyrrole, 4,5,6,7-tetrahydroindole, indole, carbazole, diisobutylaluminum-2, 5-dimethylpyrrolide, diethylaluminum 2,5-dimethylpyrrolide, dimethylaluminum-2,5-dimethylpyrrolide, diisobutylaluminum pyrrolide, diethylaluminum pyrrolide, dimethylaluminum pyrrolide and the like.

The component (D) of the catalyst used in the present invention is a group 13 (IIIB)-halogen compound represented by the general formula: MTtU3-t or a group 14 (IVB)-halogen compound represented by the general formula: M'Tt'U4-t'.

In the formula, M is an atom from the group 13 (IIIB) and M' is an atom from the group 14 (IVB). T is an alkyl group, an aryl group, an allyl group or a hydrogen atom, U is a halogen atom, t is a real number of 0 or more and less than 3 and t' is a real number of 0 or more and less than 4.

The atom from the group 13 (IIIB) includes, for example, boron, aluminum, gallium, indium and thallium, whereby aluminum is particularly preferred.

The atom from the group 14 (IVB) includes, for example, carbon, silicon, germanium, tin and lead, whereby carbon, silicon, germanium and tin are particularly preferred.

The alkyl group includes, for example, methyl group, ethyl group, propyl group, butyl group and the like.

The aryl group includes, for example, phenyl group, tolyl group, xylyl group, indenyl group, naphthyl group and the like.

The allyl group includes, for example, 1-propenyl group.

The halogen atom includes chlorine, bromine, iodine and fluorine, whereby chlorine and bromine are preferred.

The group 13 (IIIB)-halogen compound includes aluminum halide compounds such as diethylaluminum chloride, diisobutylaluminum chloride, ethylaluminum dichloride, isobutylaluminum dichloride, ethylaluminum sesquichloride and the like.

The group 14 (IVB)-halogen compound includes organic halogen compounds such as n-butyl bromide, isobutyl bromide, t-butyl bromide, n-hexyl bromide, n-octyl bromide, 1,4-dibromobutane, 1,6-dibromohexane, n-buyl chloride, isobutyl chloride, t-butyl chloride, n-hexyl chloride, n-octyl chloride, 1,4-dichlorobutane, 1,6-dichlorohexane, bromobenzene, chlorobenzene and the like, germanium halide compounds such as germanium tetrachloride and the like, tin halide compounds such as tin tetrachloride, silicon halide compounds such as trimethyl-ehlorosilane and the like, and so on.

The ratio (molar ratio) (A)/(B)/(C)/(D) is usually 1/(1–100)/(1–50)/(1–50), preferably 1/(5–75)/(1–20)/(1–30) and more preferably 1/(5–50)/(1–10)/(1–10). If the amount of (A) is too small, the activity may be insufficient. If the amount of (B) is too small, again the activity may be insufficient. If the amount of (C) is too small, then the selectivity of 1-hexene may lower.

When the components (A), (B), (C) and (D) are contacted, it is necessary to use 1-hexene as the solvent. This allows disuse of apparatus and energy for separating the desired 1-hexene. When other solvent than 1-hexene, such as for example, butane, isobutane, pentane, hexane, heptane, 1-octene, toluene, xylene, chlorobenzene, dichlorobenzene and the like is used, it will be necessary to recycle the solvent and to equip a recovering apparatus for economy purpose. In addition, a big pressure vessel for trimerization will be required correspondingly to the volume of the solvent to be used. Furthermore, excess energy will be required in order to separate the desired 1-hexene from the solvent. Thus, the use of 1-hexene as the solvent produces advantages that both the fixed expense and the working expenses are minimized.

For preparing the catalyst system used in the present invention, the components (A), (B), (C) and (D) are dissolved or suspended with stirring in 1-hexene as the solvent under an inert gas atmosphere such as nitrogen, argon and the like or reactant ethylene gas atmosphere. It is preferred that the components (A), (C) and (D) are charged first and the component (B) is added to the solution. The produced catalyst system may be used for trimerization reaction without removing 1-hexene as the solvent.

The temperature for contacting the components (A), (B), (C) and (D) is 10° C. or below, preferably –100° C. to 10° C. and more preferably –20° C. to 5° C. If the temperature is too high, the selectivity of 1-hexene may lower.

The period for contacting the components (A), (B), (C) and (D) may be suitably selected but usually from 1 minute to 24 hours. Long-term contacting may create no problem but no economical merit.

The trimerization reaction according to the present invention may be carried out in the following manner. Briefly, the above mentioned catalyst system and 1-hexene as the solvent are charged in a pressure reaction vessel and ethylene is introduced. The temperature is risen in order to initiate the reaction. The amount of the catalyst may be adjusted such that the concentration of chromium atom in the reaction mixture is preferably 0.000001 to 0.05 mole/l and more preferably 0.00001 to 0.01 mole/l. If the amount of the catalyst system is too small, the activity may be insufficient. The reaction temperature is usually 20 to 200° C. and preferably 20 to 150° C. When the reaction temperature is too low, the activity of the catalyst may also be low, and when, on the contrary, the reaction temperature is too high, the selectivity of the desired 1-hexene may lower. The pressure is usually from the atmospheric pressure to 200 $Kg/cm^2$ and preferably 10 to 100 $Kg/cm^2$. When the pressure is too low, the activity may be insufficient. The reaction period is usually from 0.1 to 8 hours and preferably 0.5 to 7 hours. When the reaction period is too short, the reactivity may be low. The recovery of the desired 1-hexene from the reaction mixture of the present invention may be accomplished by, for example, distillation.

The cataiyst system used in the present invention may be used as above or in the form of carrier-bound catalyst carried on or over an inorganic carrier such as silica, alumina, silica-alumina, zeolite, aluminum phosphate and the like or an organic carrier such as ion-exchanger resin, polystyrene, polyvinylpyridine and the like.

In the present invention, 1-hexene is used as the solvent for carrying out the trimerization reaction as described above. The solvent 1-hexene may be used in one portion from the time of preparing the catalyst system or alternatively may be added after to the solvent used for preparing the catalyst system.

The characteristic of the present invention is that the solvent for preparing the catalyst and for carrying out the trimerization is limited to 1-hexene. The reason for the limitation is described above. When the catalyst is prepared using the components (A), (B), (C) or (D) stored in a solvent other than 1-hexene, a small amount of such solvent other than 1-hexene may be contaminated in the catalyst system or trimerization reaction, but such contamination does not cause trouble insofar as the contamination of other solvent is not more than 5% by weight, for example, of 1-hexene as the solvent for trimerization reaction.

EXAMPLE

The present invention will be described with Examples, but these Examples don't limit the scope of the invention.

Example 1

Under an argon atmosphere, 20 ml of degassed and dried 1-hexene as the solvent was cooled to 2 to 3° C. in an ice-water bath and 13.4 mg (0.026 m mole) of trichlorotris (4-dimethylaminopyridine) chromium(III) (A1), 7.2 mg (0.076 m mole) of 2,5-dimethylpyrrole (C1) (9.5% by weight solution in heptane) and 14.7 mg (0.069 m mole) of germanium tetrachloride (D1) (0.8 mole/l solution in heptane) were added with stirring to form a suspension. Then, under an ethylene atmosphere, the above suspension, 85.5 mg (0.75 m mole) of triethylaluminum (B1) (1.0 mole/l solution in heptane) and 140 ml of 1-hexene as the solvent were charged into a pressure reaction vessel with an inner volume of 0.5 liter, previously cooled to 10° C. or below in an ice-water and ethylene was introduced up to a pressure of 25 $Kg/cm^2G$.

The trimerization reaction was carried out by rising temperature with stirring. The reaction temperature was 100° C., the reaction pressure 40 $Kg/cm^2G$, the reaction period 2 hours, and ethylene was supplied as required.

Solid and liquid phases in the reaction mixture were separated and the amount of the polymer product was calculated from the weight of the solid phase and analysis by gas chromatography of the liquid phase. The reaction conditions and results are shown in Table 1 and 2.

Example 2

The procedure of Example 1 was repeated except that 10.5 mg (0.026 m mole) of trichlorotris(ethylenediamine) chromium(III) 3.5 hydrate (A2) was used as the chromium compound in place of trichlorotris(4-dimethylaminopyridine) chromium(III) (A1). The reaction conditions and the results are shown in Table 1 and 2.

Example 3

The procedure of Example 1 was repeated except that 12.3 mg 0.026 m mole) of chromium(III) tris(2-ethylhexanoate) (A3) (0.8% by weight solution in heptane) was used as the chromium compound in place of trichlorotris(4-dimethylaminopyridine) chromium(III) (A1) and the reaction temperature was changed to 80° C. The reaction conditions and the results are shown in Tables 1 and 2.

Example 4

The procedure of Example 1 was repeated except that 18.6 mg (0.075 m mole) of ethylaluminum sesquichloride (D2) (1.0 mole/l solution in heptane) was used as the halogen compound in place of germanium tetracloride (D1) and the reaction period was changed to 3 hours. The reaction conditions and the results are shown in Tables 1 and 2.

Example 5

The procedure of Example 4 was repeated except that 12.3 mg (0.026 m mole) of chromium(III) tris(2-ethylhexanoate) (A3) (0.8% by weight solution in heptane) was used as the chromium compound in place of trichlorotris(4-dimethylaminopyridine) chromium(III) (A1). The reaction conditions and the results are shown in Tables 1 and 2.

Comparative Example 1

The procedure of Example 2 was repeated except that germanium tetrachloride (D1) was not used. The reaction conditions and the results are shown in Tables 1 and 2.

TABLE 1

|  | Ex. 1 | Ex. 2 | Ex. 3 | Ex. 4 | Ex. 5 | Com. Ex. 1 |
|---|---|---|---|---|---|---|
| Catalyst Component |  |  |  |  |  |  |
| Kind *1 |  |  |  |  |  |  |
| (A) | A1 | A2 | A3 | A1 | A3 | A2 |
| (B) | B1 | B1 | B1 | B1 | B1 | B1 |
| (C) | C1 | C1 | C1 | C1 | C1 | C1 |
| (D) | D1 | D1 | D1 | D2 | D2 | — |
| Composition *2 |  |  |  |  |  |  |
| (A) | 1 | 1 | 1 | 1 | 1 | 1 |
| (B) | 29 | 29 | 30 | 29 | 29 | 29 |
| (C) | 3 | 3 | 3 | 3 | 3 | 3 |
| (D) | 3 | 3 | 3 | 3 | 3 | 3 |
| Temperature for catalyst preparation (° C.) *3 | <10 | <10 | <10 | <10 | <10 | <10 |
| Amount of catalyst *4 | 0.16 | 0.16 | 0.16 | 0.16 | 0.16 | 0.16 |
| Reaction temperature (° C.) | 100 | 100 | 80 | 100 | 100 | 100 |
| Reaction Pressure Kg/cm²G | 40 | 40 | 40 | 40 | 40 | 40 |
| Reaction Period (hr) | 2 | 2 | 2 | 3 | 3 | 2 |

TABLE 2

|  | Ex. 1 | Ex. 2 | Ex. 3 | Ex. 4 | Ex. 5 | Com. Ex. 1 |
|---|---|---|---|---|---|---|
| Results |  |  |  |  |  |  |
| Activity *5 |  |  |  |  |  |  |
| g/g-Cr | 58440 | 55672 | 57922 | 92649 | 64074 | 26020 |
| g/g-Cr/hr | 29220 | 27836 | 28961 | 30883 | 21358 | 13010 |
| Selectivity % *6 |  |  |  |  |  |  |
| $C_6$-compound *7 | 79.8 | 74.8 | 70.9 | 76.4 | 60.6 | 28.3 |
| 1-hexene | 78.8 | 73.3 | 69.6 | 75.4 | 58.8 | 22.7 |
| $C_4$-compound | 0.1 | 0.2 | 0.2 | 0.2 | 1.1 | 7.0 |
| $C_8$-compound | 0.4 | 0.7 | 0.8 | 0.5 | 2.1 | 6.3 |
| $C_{10}$-compound | 17.3 | 20.9 | 22.4 | 19.4 | 26.4 | 42.2 |
| Polymer | <0.1 | 0.1 | 0.5 | <0.1 | 0.1 | 0.2 |
| Purity of 1-hexene *8 | 98.6 | 98.1 | 98.2 | 98.7 | 97.1 | 80.2 |

Notes:
*1 Catalyst Component: Kind
  A1: trichlorotris(4-dimethylaminopyridine) chromium (III)
  A2: trichlorotris(ethylenediamine) chromium(III)3.5 hydrate
  A3: chromium (III) tris(2-ethylhexanoate)
  B1: triethylaluminum
  C1: 2,5-dimethylpyrrole
  D1: germanium tetrachloride
  D2: ethylaluminum sesquichloride
*2 Catalyst Component: Composition (molar) ratio per mole component (A)
*3 Temperature for preparing catalyst is the temperature when the components (A), (B), (C) and (D) were contacted.
*4 Amount of catalyst
  concentration (m mole/l) of chromium atom in the solution charged in the pressure vessel
*5 Activity
  g/g-Cr: total products (produced 1-hexene, produced polymer and other products) amount (g) per gram chromium atom in the catalyst
  g/g-Cr/hr: total products (produced 1-hexene, produced polymer and other products) amount (g) per gram chromium atom in the catalyst per an hour
*6 Selectivity
  $C_6$-compound: (produced $C_6$-compound(g)/total product(g))×100
  1-hexene: (produced 1-hexene(g)/total product(g))×100
  $C_4$-compound: (produced $C_4$-compound(g)/total product(g))×100
  $C_8$-compound: (produced $C_8$-compound(g)/total product(g))×100
  $C_{10}$-compound: (produced $C_{10}$-compound(g)/total product(g))×100
  Polymer: (produced polymer(g)/total product(g))×100
*7 $C_6$-compound illustrated produced 1-hexene, 2-hexene, 3-hexene and produced hexane.
*8 Purity of 1-hexene: (produced 1-hexene(g)/produced $C_6$-compound(g))×100

What is claimed is:

1. A process for producing 1-hexene comprising the steps of:
  (1) preparing a catalyst system by contacting in a 1-hexene solvent the following components (A), (B), (C) and (D):
  (A) a chromium-containing compound represented by the general formula:

$$CrX_kY_m$$

wherein X is a residue of a carboxylic acid, a residue of a 1,3-diketone, a halogen atom or an alkoxyl group, k is an integer of 2 to 4, Y in Ym is an amine compound, a phosphine compound, a phosphine oxide compound, a nitrosyl group or an ether compound and m is an integer of 0 to 6, with the proviso that any two Y's may be same or different;

(B) trialkylaluminum or dialkylaluminum hydride;

(C) a pyrrole compound or a derivative thereof;

(D) a Group 13 (IIIB)-halogen compound represented by the general formula: $MTtU_{3-t}$ or a Group 14 (IVB)-halogen compound represented by the general formula: $M'T't'U_{4-t'}$ wherein M is a Group 13 (IIIB) atom, M' is a Group 14(IVB) atom, T is an alkyl group, an aryl group, an allyl group or a hydrogen atom, U is a halogen atom, t is a real number of 0 or more and less than 3 and t' is a real number of 0 or more and less than 4;

(2) charging the catalyst system in a reaction vessel without removing the 1-hexene solvent from the catalyst system;

(3) adding ethylene and a solvent to the reaction vessel; and (4) trimerizing said ethylene to form 1-hexene;

wherein said solvent added to the reaction vessel consists essentially of 1-hexene and wherein said solvent added to the reaction vessel is not removed from the 1-hexene formed by trimerization.

2. The process according to claim 1, wherein X in the component (A) is a halogen atom.

3. The process according to claim 1, wherein the component (B) is trialkylaluminum.

4. The process according to claim 1, wherein the catalyst system is obtained by first adding the components (A), (C) and (D) to the solvent and then adding the component (B).

5. The process for producing 1-hexene according to claim 1, wherein the 1-hexene solvent added to the reaction vessel is the 1-hexene solvent used to prepare the catalyst system.

6. The process for producing 1-hexene according to claim 1, wherein the 1-hexene solvent added to the reaction vessel is in addition to the 1-hexene solvent used to prepare the catalyst system.

7. The process for producing 1-hexene according to claim 1, further comprising separating the 1-hexene from the reaction mixture by distillation.

8. The process for producing 1-hexene according to claim 1, wherein the catalyst system contains not more than 5% by weight solvent other than 1-hexene, based on the total 1-hexene added to the reaction vessel.

* * * * *